(12) United States Patent
Contiliano et al.

(10) Patent No.: US 11,844,687 B2
(45) Date of Patent: Dec. 19, 2023

(54) METHODS OF MAKING IMPLANTS HAVING GEL ZONES WITH HIGHER LEVELS OF COHESIVENESS FOR ESCHEWING SCALLOPING, DIMPLING, AND WRINKLING

(71) Applicant: Mentor Worldwide LLC, Irvine, CA (US)

(72) Inventors: Joseph H. Contiliano, Somerville, NJ (US); Krasmira Hristov, Hillsborough, NJ (US); Duan Li Ou, Watchung, NJ (US); Leo B. Kriksunov, Ithaca, NY (US); Robert J. Tannhauser, Bridgewater, NJ (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 0 days.

(21) Appl. No.: 17/879,013

(22) Filed: Aug. 2, 2022

(65) Prior Publication Data
US 2022/0362007 A1    Nov. 17, 2022

Related U.S. Application Data

(62) Division of application No. 16/858,627, filed on Apr. 25, 2020, now Pat. No. 11,471,268.

(51) Int. Cl.
*A61F 2/12* (2006.01)
*A61L 27/04* (2006.01)
(Continued)

(52) U.S. Cl.
CPC .............. *A61F 2/12* (2013.01); *A61L 27/047* (2013.01); *A61L 27/16* (2013.01); *A61L 27/34* (2013.01);
(Continued)

(58) Field of Classification Search
CPC .................. A61F 2/12; A61F 2240/001; A61F 2250/0003; A61L 27/047; A61L 27/16;
(Continued)

(56) References Cited

U.S. PATENT DOCUMENTS

| 4,472,226 A | 9/1984 | Redinger et al. |
| 4,531,244 A | 7/1985 | Hamas |

(Continued)

FOREIGN PATENT DOCUMENTS

| EP | 1510189 | 2/2005 |
| EP | 3045146 | 9/2019 |

(Continued)

OTHER PUBLICATIONS

International Search Report Issued in corresponding International Application No. PCT/IB2021/053257, dated Jun. 23, 2021, 3 pages.

*Primary Examiner* — Keri J Nelson
*Assistant Examiner* — Rebecca Lynee Zimmerman
(74) *Attorney, Agent, or Firm* — TROUTMAN PEPPER HAMILTON SANDERS LLP

(57) ABSTRACT

A method of making an implantable prosthesis includes applying a gelling enhancer layer over an inner surface of a wall of a silicone shell having anterior and posterior walls surrounding an interior volume. The method includes filling the interior volume of the shell with a silicone gel and curing the silicone gel. The cured silicone gel that is located within a zone that is in the vicinity of the gelling enhancer layer has a higher level of cohesiveness than the cured silicone gel that is located outside the zone. The zone of the silicone gel having the higher level of cohesiveness has a thickness of 2-10 mm. The silicone gel located outside the zone has a first concentration level of a gelling enhancer and the silicone gel (Continued)

located within the zone has a second concentration level of the gelling enhancer that is 5%-300% greater than the first concentration level.

17 Claims, 12 Drawing Sheets

(51) Int. Cl.
*A61L 27/16* (2006.01)
*A61L 27/34* (2006.01)
*C08G 77/04* (2006.01)

(52) U.S. Cl.
CPC ........ *C08G 77/04* (2013.01); *A61F 2240/001* (2013.01); *A61F 2250/0003* (2013.01)

(58) Field of Classification Search
CPC .......... A61L 27/34; A61L 27/18; A61L 27/28; A61L 27/50; C08G 77/04
See application file for complete search history.

(56) References Cited

U.S. PATENT DOCUMENTS

| | | |
|---|---|---|
| 5,104,409 A | 4/1992 | Baker |
| 5,447,535 A | 9/1995 | Muller |
| 5,480,430 A | 1/1996 | Carlisle et al. |
| 6,228,116 B1 | 5/2001 | Edergerber |
| 6,605,116 B2 | 8/2003 | Falcon et al. |
| 8,192,486 B2 | 6/2012 | Glicksman |
| 8,858,630 B2 | 10/2014 | Maxwell et al. |
| 9,050,184 B2 | 6/2015 | Van Epps |
| 9,138,310 B2 | 9/2015 | Powell et al. |
| 9,138,311 B2 | 9/2015 | Van Epps et al. |
| 9,808,338 B2 | 11/2017 | Schuessler et al. |
| 9,918,829 B2 | 3/2018 | Van Epps et al. |
| 2003/0036803 A1 | 2/2003 | McGhan |
| 2007/0135916 A1 | 6/2007 | Maxwell et al. |
| 2008/0221679 A1 | 9/2008 | Hamas |
| 2010/0114312 A1 | 5/2010 | Glicksman |
| 2011/0046729 A1 | 2/2011 | Schuessler et al. |
| 2012/0259428 A1 | 10/2012 | Brogan et al. |
| 2013/0123918 A1 | 5/2013 | Glicksman |
| 2014/0088703 A1 | 3/2014 | Schuessler |
| 2018/0064530 A1 | 3/2018 | Glicksman |
| 2018/0186938 A1* | 7/2018 | Ou .......................... A61M 5/19 |
| 2019/0175332 A1 | 6/2019 | Schuessler et al. |
| 2021/0361402 A1* | 11/2021 | Dvir ....................... A61L 27/18 |

FOREIGN PATENT DOCUMENTS

| | | |
|---|---|---|
| WO | 2018078446 | 5/2018 |
| WO | 2018155874 | 8/2018 |
| WO | 2019159182 | 8/2019 |

* cited by examiner

| Measurement | Example 2 (Coated Region) | Example 2 (Uncoated Region) | Example 3 (Coated Region) | Example 3 (Uncoated Region) |
|---|---|---|---|---|
| Reading 1 | 28.6 | 10.4 | 29.8 | 18.4 |
| Reading 2 | 27.2 | 11.0 | 30.4 | 19.2 |
| Reading 3 | 29.2 | 10.8 | 30.8 | 18.2 |
| Reading 4 | 28.0 | 10.0 | 32.4 | 19.0 |
| Reading 5 | 26.8 | 9.8 | 30.6 | 18.0 |
| Average | 28.0 | 10.4 | 30.8 | 18.6 |

FIG. 13

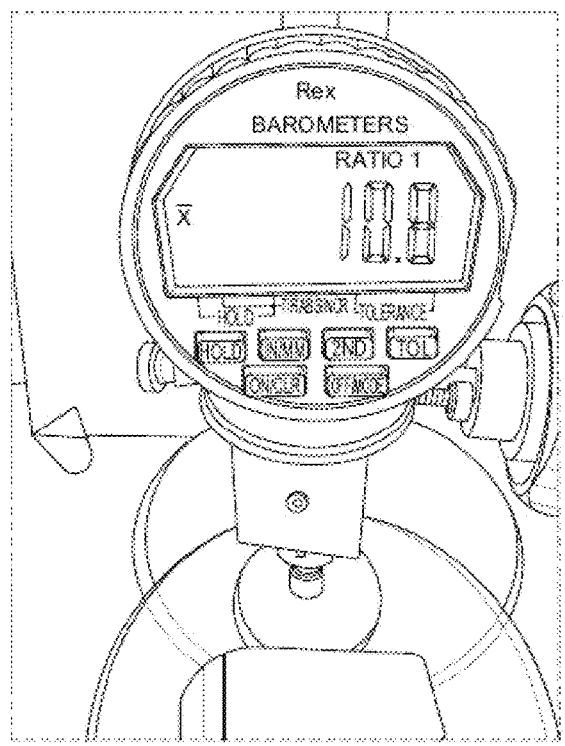
FIG. 14A
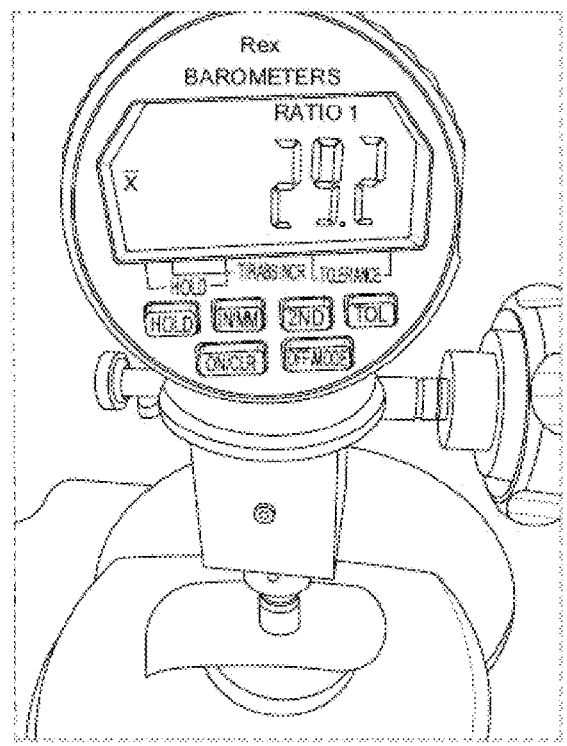
FIG. 14B
| Measurement | Example 2 (Coated Region) | Example 2 (Uncoated Region) | Example 3 (Coated Region) | Example 3 (Uncoated Region) |
|---|---|---|---|---|
| Reading 1 | 11.0 | 11.2 | 20.0 | 19.0 |
| Reading 2 | 11.2 | 11.8 | 19.2 | 19.0 |
| Reading 3 | 10.8 | 11.8 | 18.2 | 19.4 |
| Reading 4 | 11.2 | 11.4 | 19.2 | 18.4 |
| Reading 5 | 11.4 | 10.8 | 19.6 | 18.8 |
| Average | 11.1 | 11.4 | 19.2 | 18.9 |
FIG. 15

METHODS OF MAKING IMPLANTS HAVING GEL ZONES WITH HIGHER LEVELS OF COHESIVENESS FOR ESCHEWING SCALLOPING, DIMPLING, AND WRINKLING

CROSS-REFERENCE TO RELATED APPLICATIONS

The present patent application is a divisional of U.S. patent application Ser. No. 16/858,627, filed on Apr. 25, 2020, published as US 2021/0330448, now allowed, the disclosure of which is hereby incorporated by reference herein.

BACKGROUND OF THE INVENTION

Field of the Invention

The present patent application is generally related to medical devices, and is more specifically related to implantable devices such as mammary implants.

Description of the Related Art

Implantable devices, such as breast implants, are commonly used to replace or augment body tissue. In the case of the female breast, it may become necessary to remove some or all of the mammary gland and surrounding tissue in order to treat breast cancer. This type of surgery usually leaves a void that may be filled with an implantable prosthesis that supports surrounding tissue and provides a normal body appearance, eliminating much of the shock and depression that often follows breast cancer surgeries. Implantable prostheses are also used for breast augmentation procedures.

Implantable prostheses and tissue expanders usually include a shell made of silicone or a biocompatible polymer. Such devices are typically manufactured by dipping an appropriately sized and shaped mandrel into silicone. The mandrel may be solid or hollow. In other methodologies, a silicone solution may be sprayed onto the mandrel and allowed to cure. Hollow molds may also be used for forming the shells of implantable prostheses.

When a mandrel is used for making an implant, the process results in the formation of a shell having a mandrel opening, e.g., a circular hole, in one of its faces. After the shell has been formed, it must be removed from the mandrel. The mandrel opening is subsequently covered with a patch that seals the hole to form a fluid impervious implant shell. The completed shell can remain unfilled, be pre-filled, or intraoperatively filled through a small fill port or valve with a solution such as gel, saline, foam, or combinations of these materials.

In some instances, silicone breast implants are not completely filled with solution or gel. This situation may result in the formation of a crater or concavity at the apex of the implant, which is commonly referred to as the ashtray effect. The ashtray effect is generally most evident when the implant is positioned atop a flat surface.

FIG. 1 shows a conventional breast implant 50 having an apex 52 at an upper end or anterior wall thereof, a base 54 at a lower end thereof, a radius 56 that extends around the circumference of the implant, and a dome 58 having a convexly curved surface that extends between the apex 52 and the radius 56. The implant is not completely filled with gel (e.g., a silicone gel), which results in the occurrence of the undesirable ashtray effect (i.e., the presence of craters, depressions, or concavities at the apex). Many efforts have been directed to eliminate the ashtray effect including upside down curing and adding extra gel. Both approaches may increase the cost of an implant or involve expensive tooling. Adding extra gel may add weight to the implant. Moreover, in some instances, upside down curing has not been deemed to efficiently remove the ashtray effect.

Breast implants are generally designed to be relatively soft and pliable, which also makes breast implants susceptible to rippling or wrinkling. One of the primary clinical complications with breast implants is rippling, which may be discernible through the skin as ripples, of which smaller framed women with larger implants are more susceptible. FIG. 2 shows a breast implant 70 having ripples 72. Avoiding or minimizing the occurrence of ripples has become an issue of enhanced importance with the increase of pre-pec procedures whereby implants are placed above the pectoralis muscle and closer to the skin. In any event, wrinkles and rippling are not desirable and technologies to reduce or eliminate their occurrence are sought without increasing the amount of gel, increasing shell tension, and/or increasing the outer diameter of the implant.

Another problem that occurs with mammary implants is the formation of wrinkles along one or more edges of the implant, which is commonly referred to as scalloping. Referring to FIG. 3, a conventional implant 80 has an upper pole 82 and a lower pole 84. Several creases 86 are shown on the upper pole 82 of the anterior face. The creases 86 (i.e., scalloping) radiate inwardly from the perimeter 88 of the prosthesis. The creases formed in the anterior face can be discerned through the skin of the patient and are not aesthetically desirable.

In many instances it is desirable to create implant devices that maintain or increase the projection of implants without requiring an increase in the amount of gel or the gel/shell ratio. Increasing gel adds additional weight and increases the tension on the shell.

Referring to FIG. 4, in order to avoid the ashtray effect, rippling, wrinkling, and/or scalloping, and in order to improve the projection of the apex of the shell (e.g., the anterior wall of the shell), some breast implant manufacturers provide breast implants 90 that are more fully filled with gel or saline solution. Many conventional implants contain about 400 cc of gel or saline. In one design, an additional 65 cc of gel or saline is introduced into the shell. The additional gel or saline added to the shell of the implant 90 improves the projection of the apex 92 of the implant. Unfortunately, increasing the volume of gel or saline within the implant 90 adds additional weight to the implant, and increases the tension on the shell.

In view of the above state of the art, there remains a need for mammary implants and optionally tissue expanders that minimize the occurrence of the ashtray effect, rippling, wrinkling, and scalloping, while providing improved projection at the apex of the shell. In addition, there remains a need for systems, devices and methods that minimize the weight of implants. There also remains a need for implants having enhanced structural integrity, improved fatigue strength, and that maintain a soft feel to the touch.

SUMMARY OF THE INVENTION

In one embodiment, a silicone shell has an inner surface and a gelling enhancer, such as a catalyst, a cross-linker, or combination thereof, is coated on the inner surface of the silicone shell. When the silicone shell is filled with a gel and the gel is thermally cured, the gel that is close to the gelling enhancer that is coated onto the inner surface of the shell wall will have a higher level of cohesiveness (i.e., more rigid gel or gel having lesser softness or pliability), which preferably provides an implant that is less prone to dimpling, wrinkling and/or scalloping.

In one embodiment, an implant preferably includes a silicone shell and a silicone gel disposed inside the shell. In one embodiment, the implant desirably has a layer of a gelling enhancer containing material disposed on a portion of the inner surface of the wall of the shell.

In one embodiment, the gelling enhancer preferably provides for higher cohesiveness of the gel in the vicinity of the layer of the gelling enhancer overlying the inner surface of the shell, however, the cohesiveness of the gel that is remote from the gelling enhancer coating is unchanged and/or unaffected by the gelling enhancer. The higher cohesiveness gel is forming and localized to the areas immediately adjacent to the layer of gelling enhancer In one embodiment, the presence of the gelling enhancer coating preferably improves the geometry of the implant by preventing the formation of dimples, wrinkling and/or scalloping on the shell of the implant.

In one embodiment, the gelling enhancer is placed directly on the inner surface of the silicone shell prior to filling the shell with gel and/or prior to curing the gel (e.g., thermally curing).

In one embodiment, the gelling enhancer may be applied as a solution in a volatile solvent.

In one embodiment, the gelling enhancer may be a paste that is applied to the inner surface of the silicone shell.

In one embodiment, the gelling enhancer may be applied as a film or as a part of a film, or may be positioned on a film (e.g., an isolating polymeric layer) that is placed on the inner surface of the shell.

In one embodiment, a silicone shell of an implant is desirably filled with a gel material (e.g., a curable silicone gel material). In one embodiment, the implant preferably includes one or more layers of a gelling enhancer or gelling enhancer containing material that coats an inner surface of a wall (e.g., an anterior wall) of the silicone shell. The gelling enhancer preferable diffuses into the gel filling to provide the gel material with higher cohesiveness in the vicinity of the wall after curing, thus improving the geometry of the filled implant by preventing dimpling in the wall (e.g., the anterior wall or anterior portion) of the implant. In one embodiment, prior to or during curing of the gel filling, the gelling enhancer or gelling enhancer containing material that coats the inner surface of the wall of the silicone shell may diffuse into the gel filling that is disposed within the shell. The layers of a gelling enhancer or gelling enhancer containing material desirably affects the formation of silicone gel that is located within a zone that is in the vicinity of the gelling enhancer layer or extra gelling enhancer so that after curing, the silicone gel that is located within the zone that is in the vicinity of the gelling enhancer layer has a higher level of cohesiveness than the silicone gel that is located outside the zone.

In one embodiment, an implantable prosthesis preferably includes a silicone shell having an apex, a base, a radius located between the apex and the base, and a dome extending between the apex and the radius. In one embodiment, the silicone shell desirably includes an outer surface and an inner surface that surrounds an interior volume of the silicone shell, and a silicone gel material disposed within the interior volume of the silicone shell. In one embodiment, the implantable prosthesis preferably includes a layer of extra gelling enhancer or gelling enhancer containing material covering the inner surface of the silicone shell, whereby after curing, the silicone gel material that is located within a zone that is in the vicinity of the gelling enhancer layer has a higher level of cohesiveness than the silicone gel material (e.g., bulk gel) that is located outside the zone.

In one embodiment, an implantable prosthesis preferably includes a silicone shell having an apex, a base, a radius located between the apex and the base, and a dome extending between the apex and the radius. In one embodiment, the silicone shell desirably includes an outer surface and an inner surface that surrounds an interior volume of the silicone shell, and a silicone gel material disposed within the interior volume of the silicone shell. In one embodiment, the implantable prosthesis preferably includes a layer of a gelling enhancer or gelling enhancer containing material covering the inner surface of the silicone shell, whereby after curing, the silicone gel material that is located within a zone that is in the vicinity of the gelling enhancer layer has a higher level of cohesiveness than the silicone gel material that is located outside the zone, and wherein the concentration of the gelling enhancer is higher in the dome and apex regions and less toward the radius region, thus affording a tapering in gel firmness toward the radius region.

The extra gelling enhancer present on the walls of the shell results in immediately adjacent portions of the gel being exposed to more gelling enhancer resulting in gel that is cured in presence of more gelling enhancer and thus in gel with higher firmness or cohesiveness. Thus selective zones of gel inside the shell are higher in cohesiveness as compared to the bulk of the gel inside the shell.

In one embodiment, the zone of the silicone gel material having the higher level of cohesiveness has a thickness of about 2-25 mm, more preferably 2-10 mm, such as 3, 5, 10 mm.

In one embodiment, the silicone gel material that is located within the zone is more rigid than the silicone gel material that is located outside the zone.

In one embodiment, the silicone gel material that is located outside the zone has a first concentration level of the gelling enhancer and the silicone gel material that is located within the zone has a second concentration level of the gelling enhancer that is 5%-300% greater than the first concentration level of the gelling enhancer.

In one embodiment, an amount of the gelling enhancer that is disposed in the gelling enhancer layer is 5%-100% of an amount of the gelling enhancer that is disposed in the silicone gel material that is located outside the zone.

In one embodiment, the amount of the gelling enhancer that is disposed in the gelling enhancer layer is 0.05-1.0X (i.e., in the zone), whereby the amount of the gelling enhancer that is disposed in the silicone gel material (i.e., bulk gel) that is disposed within the interior volume of the silicone shell is X, and whereby a combined amount of the gelling enhancer inside the implantable prosthesis, that is disposed within the gelling enhancer layer and the silicone gel material is 1.05X-2.0X.

For example, in one embodiment, if a total amount of gelling enhancer in the bulk gel before curing is 10X mg and the total amount of the gelling enhancer on the walls of the shell before curing is 0.5X mg, the combined amount of the gelling enhancer inside the implantable prosthesis is 10.5X mg (i.e., in the bulk gel and in the zone). In another embodiment, if a total amount of gelling enhancer in the bulk gel before curing is 10X mg and the total amount of the gelling enhancer on the walls of the shell before curing is 10X mg, the combined amount of the gelling enhancer inside the implantable prosthesis is 20X mg (i.e., in the bulk gel and in the zone).

In one embodiment, the silicone gel material that is located within the zone having the higher level of cohesiveness is aligned with the apex of the silicone shell.

In one embodiment, the silicone gel material that is located within the zone having the higher level of cohesiveness is aligned with an anterior wall of the silicone shell that includes the apex and the dome of the silicone shell.

In one embodiment, the silicone gel material that is located within the zone having the higher level of cohesiveness is aligned with an anterior wall of the silicone shell that includes the dome of the silicone shell with or without the apex.

In one embodiment, the silicone gel material that is located within the zone having the higher level of cohesiveness is aligned with a radius of the silicone shell.

In one embodiment, the gel enhancing layer is preferably in proximity to an anterior wall of the silicone shell.

In one embodiment, the gel enhancing layer may be in proximity to the apex of the silicone shell.

In one embodiment, the gel enhancing layer is preferably in proximity to the dome of the silicone shell.

In one embodiment, the gel enhancing layer is desirably in proximity to the radius or a side wall of the silicone shell.

In one embodiment, the gelling enhancer comprises a catalyst that preferably includes platinum, such as a Karstedt catalyst. In one embodiment, the Karstedt catalyst desirably includes an organoplatinum compound derived from divinyl-containing disiloxane. In one embodiment, the gelling enhancer layer may include a solution of Karstedt catalyst in vinyl terminated polydimethylsiloxane.

In one embodiment, the organoplatinum compound may be derived from a d vinyl-containing disiloxane. Preferred formulas may include $Pt_2[(Me_2SiCH=CH_2)_2O]_3$; $Pt_2(1,1,3,3$-tetramethyl-1,3-divinyldisiloxane$)_3$ or Platinum(0)-1,3-divinyl-1,1,3,3-tetramethyldisiloxane.

In one embodiment, the concentration level of the gelling enhancer in the gelling enhancer layer is about 0.01-10 $mg/cm^2$.

In one embodiment, the implantable prosthesis may include an isolating polymeric layer or polymer film located between the inner surface of the silicone shell and the gelling enhancer layer that covers the inner surface of the silicone shell. In one embodiment, the isolating polymeric layer is preferably adapted to slow down diffusion of the gelling enhancer in the gelling enhancer layer into the silicone shell.

In one embodiment, the gelling enhancer is coated, immobilized, and/or functionalized to the surface of the isolating polymeric layer and is facing toward the silicone gel material that fills the shell.

In one embodiment, the gelling enhancer layer may be applied to a first surface of the isolating polymeric layer and a second surface of the isolating polymeric layer may be applied to the inner surface of the silicone shell.

In one embodiment, an implantable prosthesis preferably includes a silicone shell having an anterior wall and a posterior wall that surround an interior volume of the silicone shell, and a silicone gel material disposed within the interior volume of the silicone shell. In one embodiment, the implantable prosthesis preferably includes a layer of a gelling enhancer covering an inner surface of the anterior wall of the silicone shell, whereby the silicone gel material that is located within a zone that is in the vicinity of the gelling enhancer layer has a higher level of cohesiveness than the silicone gel material that is located outside the zone.

In one embodiment, the implantable prosthesis preferably includes an isolating polymeric layer of film located between the inner surface of the anterior wall of the silicone shell and the gelling enhancer layer covering the inner surface of the anterior wall of the silicone shell. The isolating polymeric layer is desirably adapted to slow down diffusion of the gelling enhancer that is within the gelling enhancer layer into the silicone shell wall.

In one embodiment, a method of making an implantable prosthesis preferably includes applying a layer of a gelling enhancer over an inner surface of an anterior wall of a silicone shell, whereby the silicone shell includes the anterior wall and a posterior wall that surround an interior volume of the silicone shell, and filling the interior volume of the silicone shell with a silicone gel.

In one embodiment, the method of making the implantable prosthesis preferably includes, after the filling step, thermally curing the silicone gel disposed within the interior volume of the silicone shell for curing the silicone gel so that the cured silicone gel that is located within a zone that is in the vicinity of the gelling enhancer layer has a higher level of cohesiveness than the cured silicone gel that is located outside the zone.

In one embodiment, the step of applying a layer of a gelling enhancer preferably includes applying the gelling enhancer layer to a first surface of an isolating polymeric layer or film, and, before or after applying the gelling enhancer layer, applying a second surface of the isolating polymeric layer to the inner surface of the anterior wall of the silicone shell so that the isolating polymeric layer is disposed between the inner surface of the anterior wall of the silicone shell and the gelling enhancer layer.

These and other preferred embodiments of the present patent application will be described in more detail below.

BRIEF DESCRIPTION OF THE DRAWINGS

FIG. 13 is a chart showing the results of softness tests conducted on bottom sides of silicone slabs having regions that are coated with a layer of a gelling enhancer and regions that are uncoated, in accordance with one embodiment of the present patent application.

FIG. 14A shows a durometer gauge measuring an uncoated region of the bottom side of a silicone slab, in accordance with one embodiment of the present patent application.

FIG. 14B shows a durometer gauge measuring a gelling enhancer coated region of the bottom side of a silicone slab, in accordance with one embodiment of the present patent application.

FIG. 15 is a chart showing the results of softness tests conducted on the top side of silicone slabs opposite the regions that are coated with a layer of a gelling enhancer and regions that are uncoated, in accordance with one embodiment of the present patent application.

DETAILED DESCRIPTION OF PREFERRED EMBODIMENTS

Figure 1:
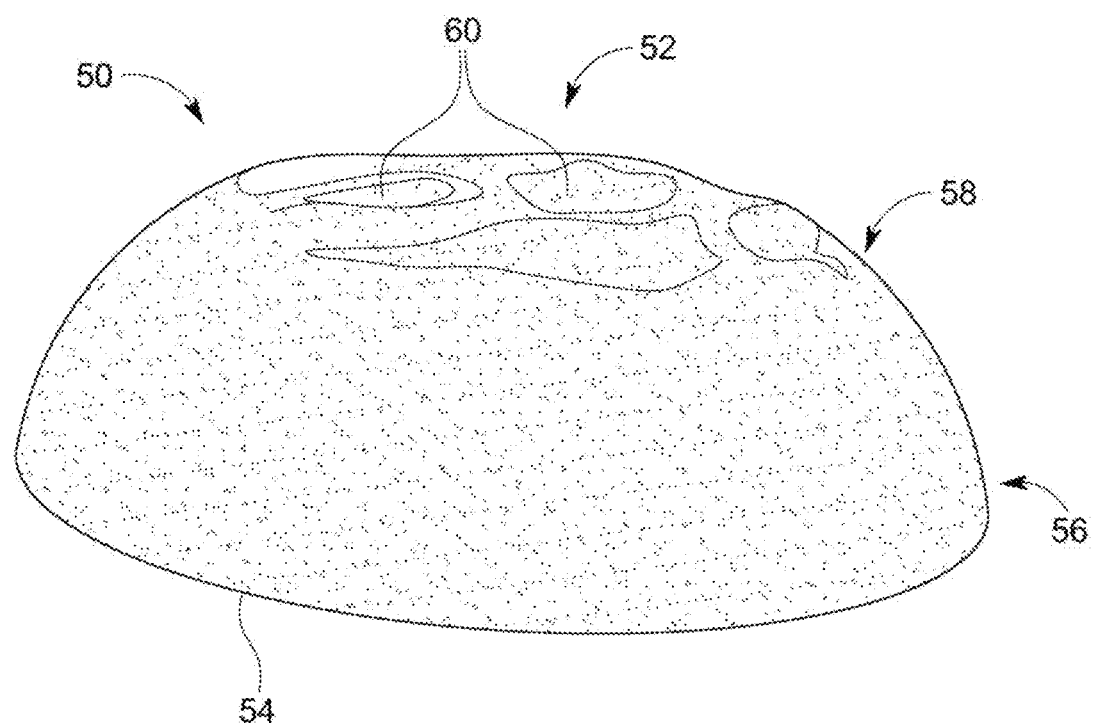
FIG. 1 shows a prior art implant having concavities at the apex of the shell.
Figure 2:
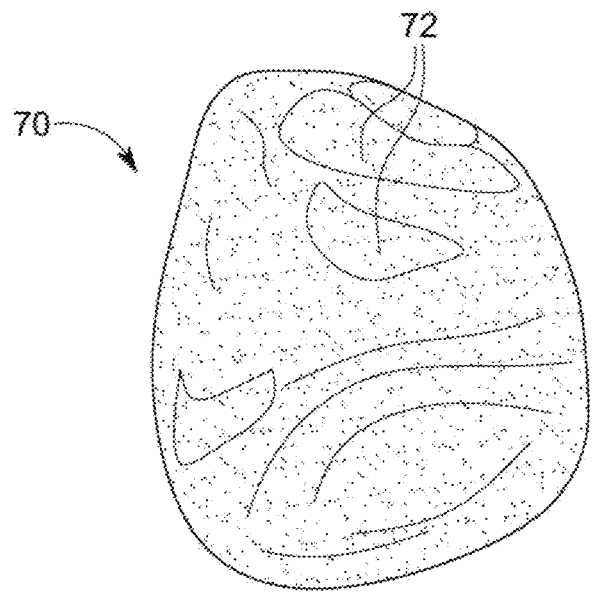
FIG. 2 shows a prior art implant rippling of the shell.
Figure 3:
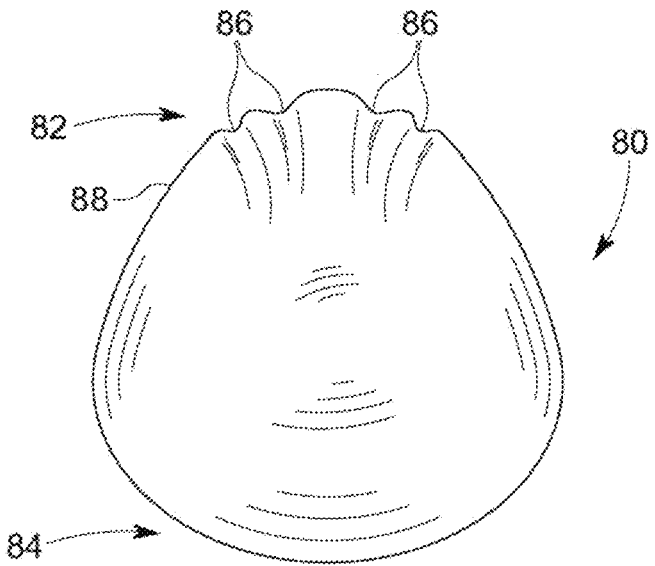
FIG. 3 shows a prior art implant with scalloping at an edge of the shell.
Figure 4:
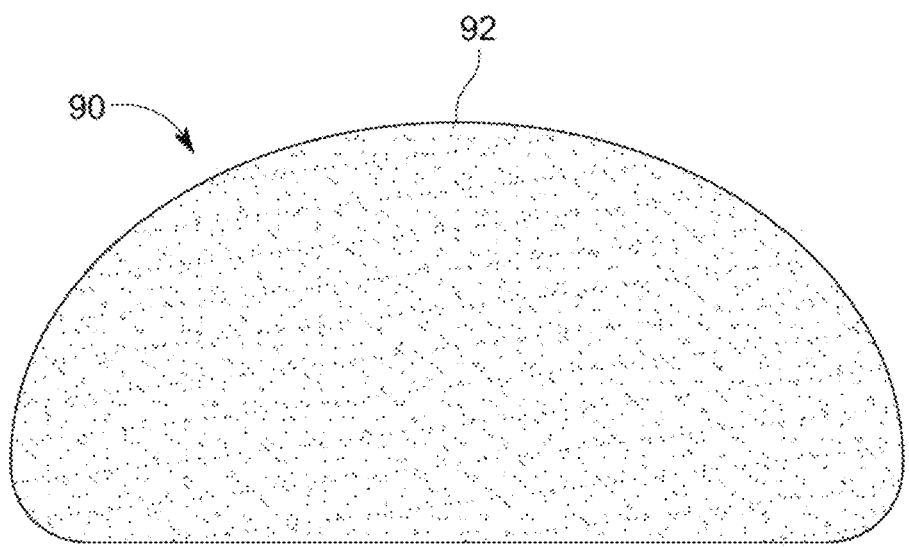
FIG. 4 shows a prior art implant having additional gel inserted into the shell to increase the projection at the apex of the shell.

In one embodiment, the elements of mammary implants disclosed herein may be defined as set forth below.

Apex. The top of a dome of a shell. The apex may be located within the top or the anterior region of the shell.

Base. The bottom or posterior region of the shell.

Gelling enhancer. A gelling enhancer or gelling enhancing compound (or several compounds) acts as accelerator of cross-linking, enhancer of cross-linking, enhancer of density of cross-linking, facilitator of gelling and or curing of the silicone gel. The presence of the gelling enhancer results in higher degree of cross-linking, and denser, more cohesive gel. Gelling enhancer is exemplified by a) catalyst that catalyzes the cross-linking reaction; b) cross-linker compound; c) Cure inhibitor scavenger, that inhibits or binds cure inhibitors and thus accelerates and densities cross-linking; d) combination or mixture of any two of a, b, and c; e) all three of a, b, and c; e) any of a through e, with the addition of excipient, binder, diluent, solvent, functional, or non-functional silicone molecules, and combinations thereof. In one embodiment, gelling enhancer comprises a catalyst of cross-linking. In another embodiment, gelling enhancer comprises the catalyst of cross-linking mixed with functional silicones. In another embodiment, gelling enhancer comprises the catalyst of cross-linking mixed with the cross-linker. In another embodiment, gelling enhancer comprises the catalyst of cross-linking mixed with cross-linker and with functional silicones. The cross-linker can be hydrogen-functional crosslinker or Si—H functional cross-linker. The functional silicone can be vinyl functional polymer. For example, Addition Curable system can be used as a filler of the implant, such as systems available from Nusil/Avantor, (Avantor Performance Materials, 100 Matsonford Road, Radnor, PA). Additional cured silicone elastomers are commonly referred to as platinum catalyzed silicones and are generally two-part systems with each part containing different functional components. These two component systems can be formulated in various ratios, with the most common ratios being 10:1 and 1:1. Generally, the Part A component contains vinyl functional silicones and the platinum catalyst, whereas Part B contains vinyl functional polymer, hydrogen-functional crosslinker, and cure inhibitor. Cure inhibitors are additives used to adjust the cure rate of the system. The cure chemistry involves the direct addition of the Si—H functional crosslinker to the vinyl functional polymer forming an ethylene bridge crosslink. The vulcanization of addition cured silicone elastomers can be heat accelerated.

In some embodiments, catalyst as a small molecule will have higher diffusion rates into the bulk of gel and effect gelling enhancement of the bulk gel. In some embodiments, the Part A1 component, that comprises vinyl functional silicones and the platinum catalyst, is used as a gelling enhancer, while a mixture of Part A and Part B is used a s bulk gel, wherein Part B comprises vinyl functional polymer, hydrogen-functional crosslinker, and optional cure inhibitor. In one embodiment, Part A1 component can have the same concentration of catalyst as Part A. In an alternative embodiment, Part A2 component, that comprises vinyl functional silicones and the platinum catalyst and is used as a gelling enhancer, has a higher concentration of catalyst vs. Part A component.

Catalyst is generally defined as a substance that increases the rate of a chemical reaction without itself undergoing any permanent chemical change. Catalyst can be present in a range of concentrations, such as 1-300 ppm, such as 10-100 ppm.

Device. A mammary implant, which is filled with gel. A device may be pre-filled, filled intraoperatively, or may be filled in situ. Breast implants are typically pre-filled.

Dome. The rounded region of the shell running from the apex of the shell to a radius region of the shell. At least a portion of the dome may be located within the anterior region of the shell.

Gel. A curable material, such as a silicone gel, used to fill the shell. As an example, the cross-linkable siloxane polymers useful as gel filling have reactive functionalities or terminal functional groups, including but not limited to vinyl terminated, hydroxyl and acrylate functional groups. The cross-linkable siloxane polymers that can be used preferably include vinyl terminated polydialkylsiloxane or vinyl terminated polyalkoarylsiloxane. Examples include but are not limited to the following vinyl terminated siloxane polymers: polydimethyl siloxane, polydiphenylsilane-dimethylsiloxane copolymer, polyphenylmethylsiloxane, polyfluoropropylmethyl-dimethylsiloxane copolymerand polydiethylsiloxane. It is particularly preferred to use vinyl terminated cross-linkable polymethyl siloxane.

The cross-linking agents that can be used include conventional silicone cross-linking agents such as, for example, polymethylhydrosiloxane, polymethylhydro-co-polydimethylsiloxane, polyethyhydrosiloxane, polymethylhydrosiloxane-co-octylmethylsiloxane, polymethylhydrosiloxane-co-methylphenylsiloxane. One preferred conventional crosslinker for use in the coatings of the present invention is polymethylhydro siloxane. The cross-linked polymer is formed by a reaction between the functionalized cross-linkable polymer and the cross-linking agent, for example, a vinylsilylation reaction between vinyl-terminated polydimethylsiloxane and polymethylhydrosiloxane optionally in the presence of a platinum complex catalyst. An example of crosslinker includes, but is not limited to, Gelest Product Code No. HMS-991, HMS-992, available from Gelest, Inc., Morrisville, PA Polymethylhydro-co-polydimethylsiloxane can also be used as crosslinker. Examples of this polymer include, but are not limited to, Gelest Product Code No. HMS-301, HMS-501.

Radius. The side region of the shell where a dome of the shell comes down to intersect with the base of the shell.

Shell. The outer envelope of the device, which contains the gel. The shell is typically made of biocompatible polymers such as silicone, however, other materials may be used.

Figure 5:
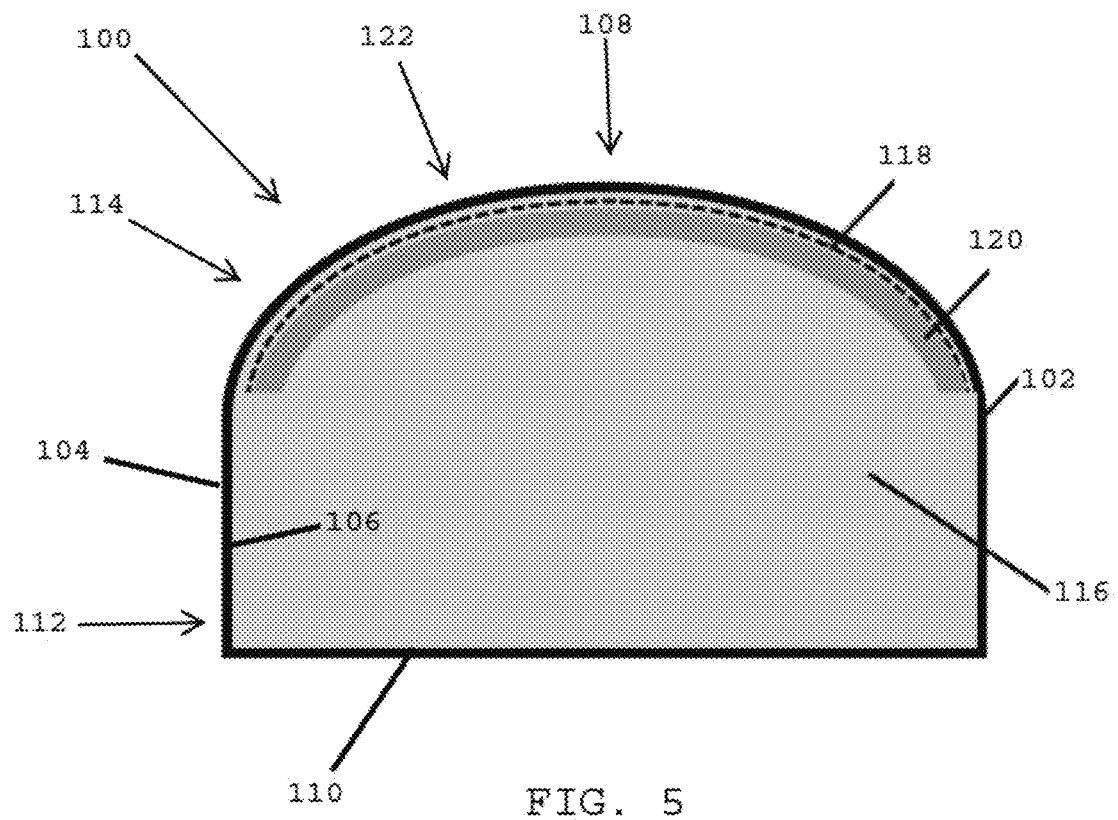
FIG. 5 is a cross-sectional view of an implant shell having a layer of a gelling enhancer and a zone aligned with an anterior wall of the implant shell in which silicone gel has a higher level of cohesiveness than silicone gel located outside the zone, in accordance with one embodiment of the present patent application.

Referring to FIG. 5, in one embodiment, a shell 100 (e.g., a silicone shell) preferably includes a shell wall 102 having an outer surface 104 and an inner surface 106. The shell 100 preferably includes an apex 108, a base 110, a radius 112 that extends around the circumference or side of the shell 100, and a dome 114 that extends from the apex 108 to the radius 112 of the shell 100. The apex 108 and the dome 114 portions of the shell 100 may define an anterior wall of the shell and the base 110 may define a posterior wall of the shell.

In one embodiment, the shell 100 may be filled with a gel 116 (e.g., a silicone gel). In one embodiment, a portion of inner surface 106 of the shell wall 102 is preferably coated with a gelling enhancer layer 118, which contains a gelling enhancer material that is adapted to interact with the gel 116 that is in the immediate vicinity of the gelling enhancer layer 118 to form a zone 120 of gel material that has a higher level of cohesiveness than the remainder of the gel 116 that fills the shell 100.

The zone 120 of the gel material having the higher level of cohesiveness is preferably formed due to presence of the gelling enhancer layer 118 that coats the inner surface 106 of the outer wall 102 of the shell 100. The higher gel cohesiveness zone 120 is preferably the region of the gel that is in the immediate vicinity the gelling enhancer layer 118, and represents an area of silicone gel having higher cohesiveness and/or higher cross-linking and/or higher viscosity than the gel 116 that is further away from the gelling enhancer layer 118 and that fills the remainder of the shell 100. The higher gel cohesiveness zone 120 can have a gradient of gel cohesiveness across the zone 120, whereby the gel 116 within the zone 120 that is closest to the extra gelling enhancer layer 118 has highest cohesiveness, while the gel 116 within the zone 120 that is farthest from the extra gelling enhancer layer 118 has cohesiveness close to or approaching the cohesiveness of the bulk gel 116.

Referring to FIG. 5, in one embodiment, an entire anterior region 122 of the shell wall 102 may be coated with the gelling enhancer layer 118. Thus, the higher gel cohesiveness zone 120 spans the entire anterior region 122 of the shell wall 102. In other embodiments, the exact location where the gelling enhancer layer is applied to the inner surface of the shell wall may be moved to a different location on the shell for changing the location of the higher gel cohesiveness zone.

The zone 120 having the higher level of cohesiveness preferably enhances the structural integrity and stability of the shell 100 to enhance projection of the apex 108 and dome 114 of the shell wall 102, thereby minimizing the occurrence of the ashtray effect, rippling, wrinkling, and/or scalloping.

Providing implant shells having zones with higher levels of cohesiveness preferably improves form stability or the ability of an implant to maintain its shape. The zone patterns disclosed herein preferably increase strength and rigidity without increasing the shell wall thickness, thus maintaining softness while improving form stability. Increasing the coverage areas of the gelling enhancer layers may greatly influence the form stability. Gelling enhancer layers may extend radially between the apex and the radius of the shell, and/or circumferentially around the sides of the implant.

In one embodiment, a shell may be made using one or more of the systems, devices and methods disclosed in U.S. Pat. No. 4,472,226 to Redinger et al. or U.S. Patent Application Publication No. US 2014/0088703 to Schuessler, the disclosures of which are hereby incorporated by reference herein.

In one embodiment, the gelling enhancer that is applied over the inner surface 106 of the shell wall 102 of the shell 100 may be any formulation of catalyst that catalyzes the gel filing. In one embodiment, the gelling enhancer may include platinum containing catalysts, such as a Karstedt catalyst. A Karstedt catalyst is an organoplatinum compound derived from divinyl-containing disiloxane. Formulas include Pt2[(Me2SiCH=CH2)2O]3; Pt2(1,1,3,3-tetramethyl-1,3-divinyldisiloxane)3; and/or Platinum(0)-1,3-divinyl-1,1,3,3-tetramethyldisiloxane. In one embodiment, the gelling enhancer may be a solution of a Karstedt catalyst in vinyl terminated polydimethylsiloxane. In one embodiment, the gelling enhancer may include catalyst and/or crosslinker formulations sold by Gelest, Avantor, Nusil, Johnson Matthey Chemical Products, Sigma-Aldrich, and other suppliers.

In one embodiment, the gelling enhancer layer 118 may be applied as a solvent based (such as xylene) gelling enhancer composition, whereby the solvent is allowed to evaporate. Additionally, or alternatively, in one embodiment, the gelling enhancer may be applied in a mixture with silicone composition and/or solvent, and allowed to at least partially dry or cure.

In one embodiment, the gelling enhancer that is applied over the inner surface 106 of the shell wall 102 of the shell 100 may be any formulation of crosslinker, such as hydrogen-functional crosslinker or Si—H functional crosslinker that crosslinks functional silicone such as vinyl functional polymer comprising the gel filing. In one embodiment, the gelling enhancer may be a solution of Si—H functional crosslinker in vinyl terminated polydimethylsiloxane.

In one embodiment, the gelling enhancer layer 118 may be applied as a solvent based (such as xylene) crosslinker composition, whereby the solvent is allowed to evaporate. Additionally, or alternatively, in one embodiment, the crosslinker may be applied in a mixture with silicone composition and/or solvent, and allowed to at least partially dry or cure.

In one embodiment, the gelling enhancer that is applied over the inner surface 106 of the shell wall 102 of the shell 100 may be any formulation of crosslinker in combination with catalyst, optionally applied in a mixture with silicone composition and/or solvent, and allowed to at least partially dry.

In one embodiment, the gelling enhancer layer preferably contains extra gelling enhancer and creates a higher concentration of the gelling enhancer in the immediate proximity to the layer 118, thus exposing the silicone gel that is in the proximity of the gelling enhancer layer 118 to excess gelling enhancer. In certain embodiments, the gelling enhancer layer 118 may contain coating levels of about 0.01-10 mg/cm$^2$ of gelling enhancer. The gel 116 located in the zone 120, after curing, can contain from about 1% to about 300% more gelling enhancer compared to the bulk gel 116 that is remote from zone 120, such as contain from 10% to 200% more gelling enhancer, such as 10, 20, 30, 50, 75, 100% more gelling enhancer compared to bulk gel gelling enhancer concentration after curing.

In embodiments, the total amount of gelling enhancer present in the gel when filling the shell is X mg, the amount of gelling enhancer disposed on the internal shell wall is from 0.05X to about 1X, so that the total amount of gelling enhancer present in the gel after curing is from about 1.05X to about 2X, and more preferably 1.1X, 1.2X, 1.3X.

A high gel cohesiveness area 120, representing a zone in the immediate vicinity of the gelling enhancer layer 118, and in proximity to the anterior region 122 of the shell wall 102 is shown in FIG. 5 and schematically represents area of the silicone gel 116 having higher cohesiveness and/or higher cross-linking and/or higher viscosity than the bulk gel 116. The higher cohesiveness area 120 is formed due to the presence of the gelling enhancer material 118. Higher cohesiveness area 120 is schematically shown as being uniform, however, the higher cohesiveness area 120 may have more of a gradient of cohesiveness, with the highest cohesiveness of gel within an area immediately adjacent or in contact with the gelling enhancer coating 118, with the cohesiveness of the gel gradually decreasing further and further from the shell wall 102 and becoming substantially the same as the cohesiveness of the bulk gel 116 at a distance from the shell wall 102 of about 5-20 mm, and more preferably about 10 mm.

Figure 6A:
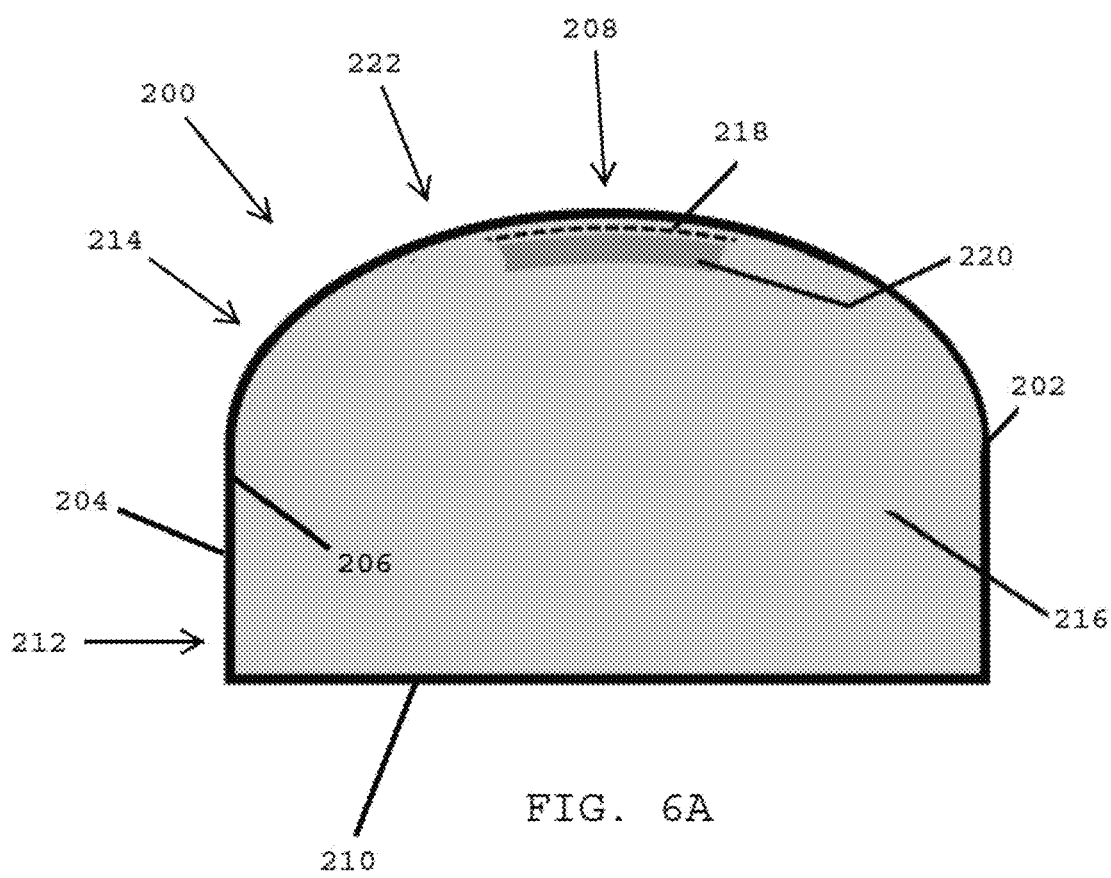
FIG. 6A is a cross-sectional view of another implant shell having a layer of a gelling enhancer and a zone aligned with an apex of the implant shell in which silicone gel has a higher level of cohesiveness than silicone gel located outside the zone, in accordance with one embodiment of the present patent application.

As noted above, the exact location of the gel having the higher level of cohesiveness may be modified by changing the location or the area where the gelling enhancer layer is applied to the inner surface of the shell wall. Referring to FIG. 6A, in one embodiment, a shell 200 (e.g., a silicone shell) preferably includes a shell wall 202 having an outer surface 204 and an inner surface 206. The shell wall 202 preferably includes an apex 208, a base 210, a radius 212 that extends around the circumference or side of the shell 200, and a dome 214 that extends from the apex 208 to the radius 212 of the shell 200.

In one embodiment, the shell 200 is filled with a gel 216 (e.g., a silicone gel). In the embodiment of FIG. 6A, a smaller area of the anterior region 222 of the inner surface 206 of the shell wall 202 (relative to the area of gelling enhancer coverage shown in FIG. 5) is coated with a gelling enhancer layer 218. The gelling enhancer later 218 contains a gelling enhancer material that is adapted to interact with a the gel that is in the immediate vicinity of the gelling enhancer layer 218 to form a zone 220 of gel material that has a higher level of cohesiveness than the remainder of the gel 216 that fills the shell 200.

The zone 220 of the gel material having the higher level of cohesiveness is preferably formed due to the presence of the gelling enhancer layer 218 that coats the inner surface of the shell. The zone 220 having the higher level of gel cohesiveness is preferably the region of the gel that is in the immediate vicinity the gelling enhancer layer 218, and represents an area of silicone gel having higher cohesiveness and/or higher cross-linking and/or higher viscosity than the gel 216 that fills the remainder of the shell 200.

Figure 6B:
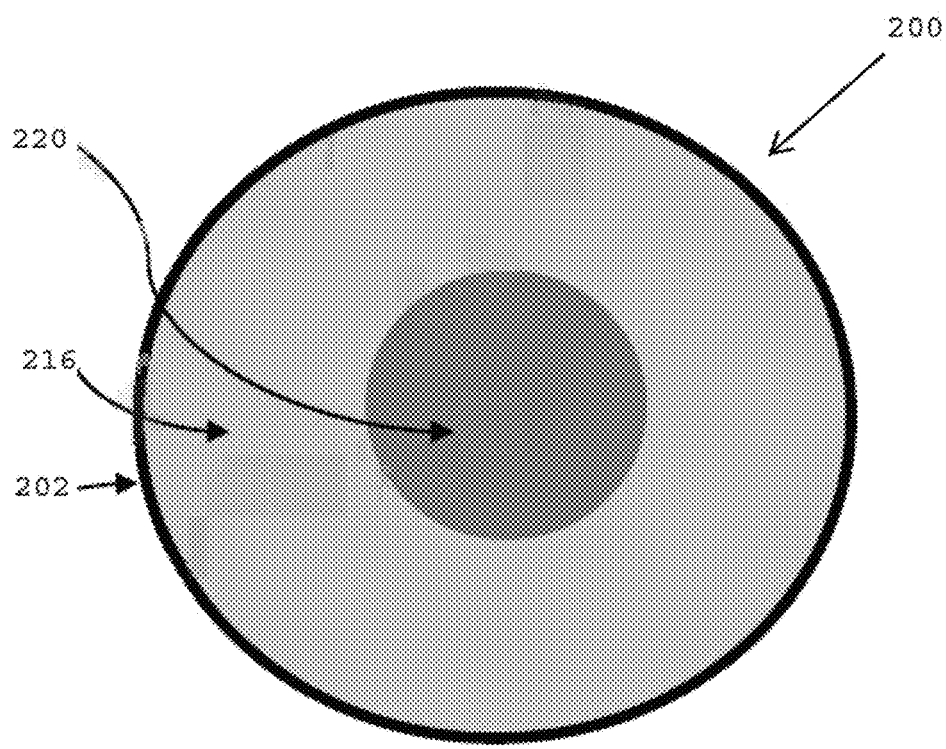
FIG. 6B is a top view of the implant shell shown in FIG. 6A.

Referring to FIG. 6B, in one embodiment, the zone 220 of the gel material that has a higher level of cohesiveness covers a smaller area of the anterior region 222 (FIG. 6A) of the inner surface 206 of the shell wall 202 relative to the area of gelling enhancer coverage shown in FIG. 5. In the embodiment of FIG. 6B, the zone 220 has a circular shape.

Figure 6C:
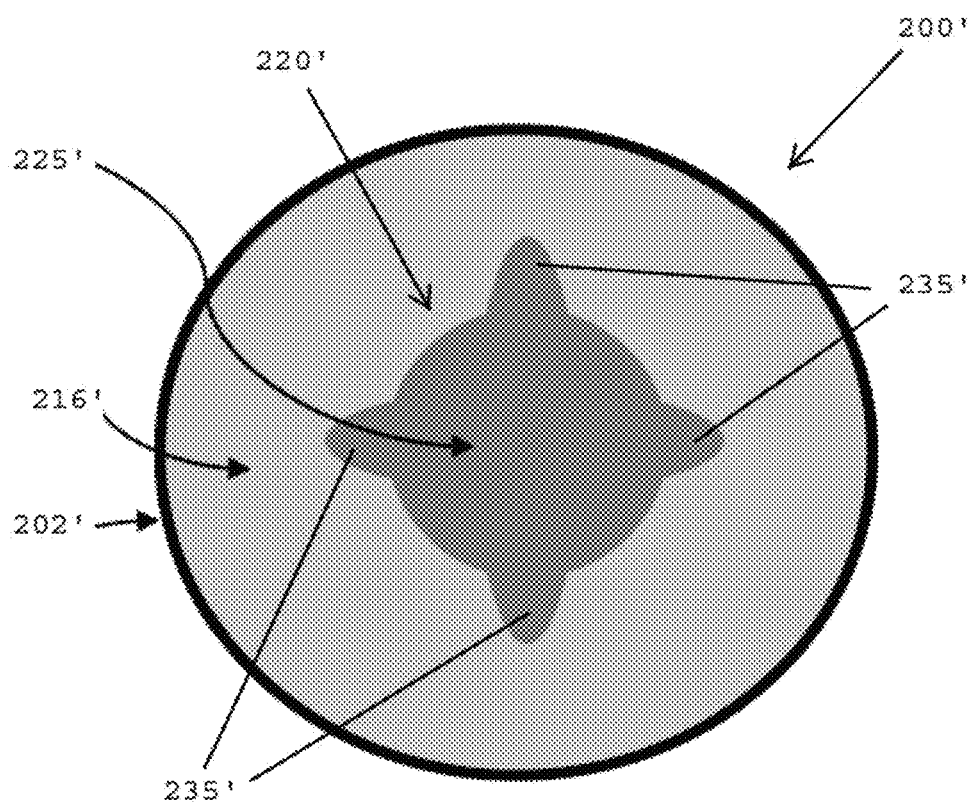
FIG. 6C is a top view of an implant shell with a non-circular shaped zone of silicone gel material that has a higher level of cohesiveness than silicone gel located outside the non-circular shaped zone, in accordance with one embodiment of the present patent application.

In one embodiment, a zone of gel material that has a higher level of cohesiveness may have a shape that is non-circular, such as an elongated shape, a cruciform shape, an elliptical shape, and/or any other geometric shape that may be formed on a shell wall of a shell. Referring to FIG. 6C, in one embodiment, a shell 200' has a shell wall 202' that contains a gel 216'. The shell 200' preferably includes a zone 220' of gel material that has a higher level of cohesiveness than the gel 216' that fills the remainder of the shell 200'. The zone 220' preferably includes a central region 225' and spurs 235' that project outwardly from the central region 225'.

Figure 7:
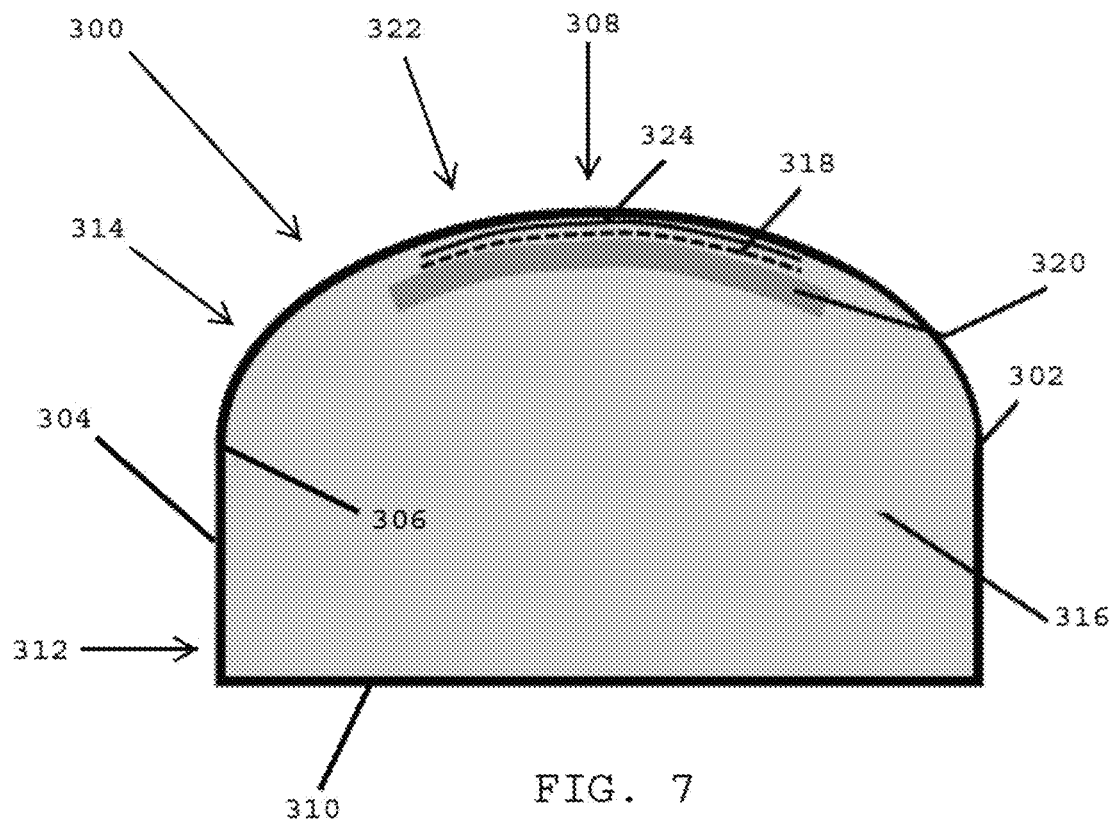
FIG. 7 is a cross-sectional view of an implant shell having a layer of a gelling enhancer, an isolating polymeric layer or film, and a zone aligned with an anterior wall of the implant shell in which silicone gel has a higher level of cohesiveness than silicone gel located outside the zone, in accordance with one embodiment of the present patent application.

Referring to FIG. 7, in one embodiment, a shell 300 (e.g., a silicone shell) preferably includes a shell wall 302 having an outer surface 304 and an inner surface 306. The shell wall 302 preferably includes an apex 308, a base 310, a radius 312 that extends around the circumference or side of the shell 300, and a dome 314 that extends from the apex 308 to the radius 312 of the shell 300.

In one embodiment, the shell 300 is filled with a gel 316 (e.g., a silicone gel). In the embodiment of FIG. 7, the anterior region 322 of the inner surface 306 of the shell wall 302 is coated with a gelling enhancer layer 318. The gelling enhancer layer 318 contains a gelling enhancer material that is adapted to interact with a the gel that is in the immediate vicinity of the gelling enhancer layer 318 to form a zone 320 of gel material that has a higher level of cohesiveness than the gel 316 that fills the remainder of the shell 300.

The zone 320 of the gel material having the higher level of gel cohesiveness is preferably formed due to presence of the gelling enhancer coating 318. The higher gel cohesiveness zone 320 is preferably the region of the gel that is in the immediate vicinity the gelling enhancer layer 318, and represents an area of silicone gel having higher cohesiveness and/or higher cross-linking and/or higher viscosity than the gel 316 that fills the remainder of the shell 300.

In one embodiment, the shell 300 preferably includes an intermediate isolating polymeric layer or film 324 that is positioned between the inner surface 306 of the shell wall 302 and the gelling enhancer layer 318. In one embodiment, the gelling enhancer layer 318 may be applied over a surface of the isolating polymeric layer 324, which, in turn, is disposed over the inner surface 306 of the shell wall 302. In one embodiment, the isolating polymeric layer 324 may be any polymer layer or coating that substantially prevents or slows down diffusion of the gelling enhancer 318 into the shell 300. Materials that may be used for forming the isolating polymeric layer 324 preferably include Polyethylene terephthalate, polyester, polypropylene, polyethylene, silicone coated with impermeable coatings such as metallized coatings, such as aluminum or silver metallized, coatings based on silica, alumina, or any materials showing low permeability to the gelling enhancer.

Optionally, the isolating polymeric layer or film 324 should have elastic properties that are equal to or greater than that of the shell material. Optionally, such materials could be designed to expand easily, such as having fenestrations or openings or apertures that improve expandability of these films.

Figure 8:
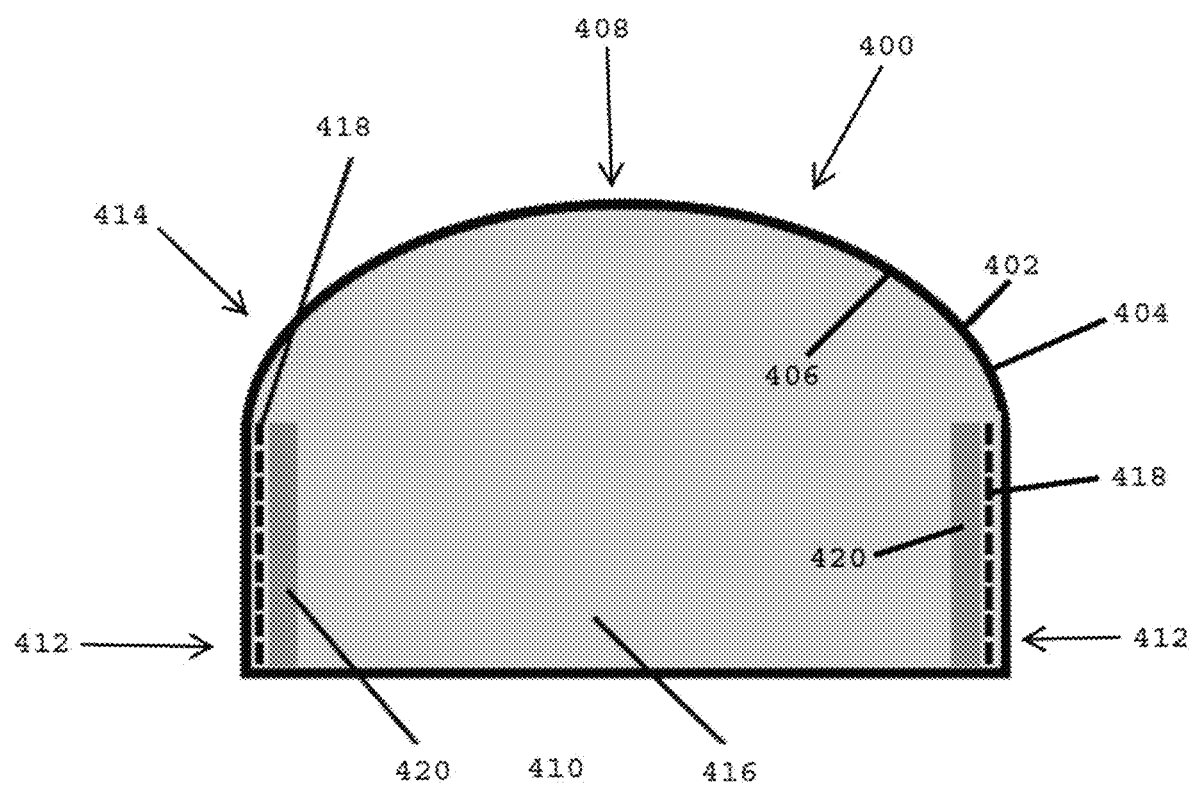
FIG. 8 is a cross-sectional view of an implant shell having a layer of a gelling enhancer and a zone aligned with a side wall of the implant shell in which silicone gel has a higher level of cohesiveness than silicone gel located outside the zone, in accordance with one embodiment of the present patent application.

In one embodiment, the zone of the gel having the higher level of cohesiveness may be located at the side and/or radius of a shell. Referring to FIG. 8, in one embodiment, a shell 400 preferably includes a shell wall 402 having an outer surface 404 and an inner surface 406. The shell wall 402 preferably includes an apex 408, a base 410, a radius 412 that extends around the circumference or side of the shell 400, and a dome 414 that extends from the apex 408 to the radius 412 of the shell 400.

In one embodiment, the shell 400 may be filled with a silicone gel 416. In one embodiment, the radial region 412 of the inner surface 406 of the shell wall 402 is preferably coated with a gelling enhancer layer 418, which contains a gelling enhancer material that is adapted to interact with the gel 416 that is in the immediate vicinity of the gelling enhancer layer 418 to form a zone 420 of gel material that has a higher level of cohesiveness than the gel 416 that fills the remainder of the shell 400. Gel cohesiveness is a characteristic of the gel related to its firmness, flowability, durometer. Gels of higher cohesiveness are firmer and more resilient, less flowable, and less soft. More cohesive gels are formed by more cross-links between gel molecules, resulting in implants with better retention of shape that are less prone to folding, collapse and retain shape better.

The higher gel cohesiveness zone 420 is preferably located at the region of the gel that is in the immediate vicinity of the gelling enhancer layer 418, and represents an area of silicone gel having higher cohesiveness and/or higher cross-linking and/or higher viscosity than the gel 416 that fills the remainder of the shell 400.

Referring to FIG. 8, in one embodiment, the radial region 412 of the shell wall 402 is coated with the gelling enhancer layer 418, and higher gel cohesiveness zone 420 spans the radial region 412 of the shell wall 402 of the shell 400.

Figure 9:
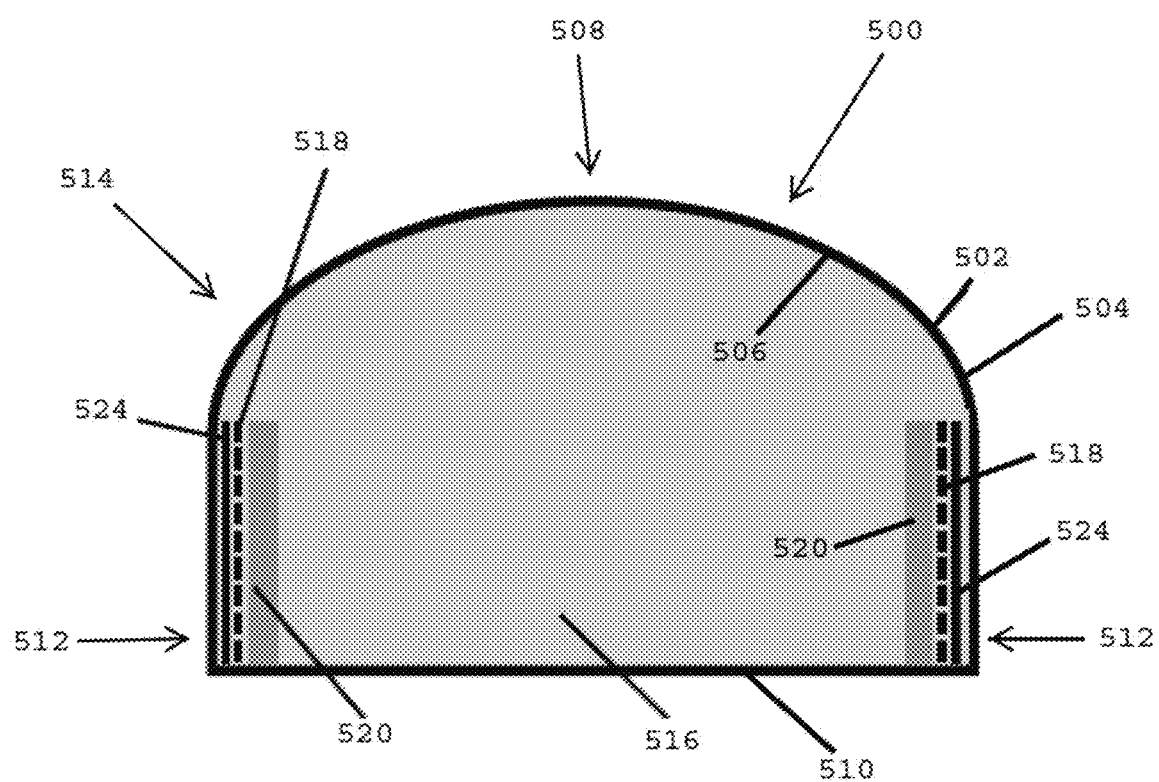
FIG. 9 is a cross-sectional view of an implant shell having a layer of a gelling enhancer, an isolating polymeric layer, and a zone aligned with a side wall of the implant shell in which silicone gel has a higher level of cohesiveness than silicone gel located outside the zone, in accordance with one embodiment of the present patent application.

Referring to FIG. 9, in one embodiment, a shell 500 preferably includes a shell wall 502 having an outer surface 504 and an inner surface 506. The shell wall 502 preferably includes an apex 508, a base 510, a radius 512 that extends around the circumference or side of the shell 500, and a dome 514 that extends from the apex 508 to the radius 512 of the shell 500.

In one embodiment, the shell 500 is filled with a gel 516 (e.g., a silicone gel). In the embodiment of FIG. 9, the radial region 512 of the inner surface 506 of the shell wall 502 is coated with a gelling enhancer layer 518. The gelling enhancer layer 518 contains a gelling enhancer material that is adapted to interact with the gel that is in the immediate vicinity of the gelling enhancer layer 518 to form a zone 520 of gel material that has a higher level of cohesiveness than the gel 516 that fills the remainder of the shell 500.

The zone 520 of the gel material having the higher gel cohesiveness is preferably formed due to presence of the gelling enhancer coating 518. The higher gel cohesiveness zone 520 is preferably the region of the gel that is in the immediate vicinity the gelling enhancer layer 518, and represents an area of silicone gel having higher cohesiveness and/or higher cross-linking and/or higher viscosity than the remainder of the gel 516 that fills the shell 500.

In the embodiment of FIG. 9, the shell 500 may include an intermediate isolating polymeric layer or film 524 that is preferably positioned between the inner surface 506 the shell wall 502 and the gelling enhancer layer 518. In one embodiment, the gelling enhancer layer 518 may applied over a surface of the isolating polymeric layer 524, which, in turn, is disposed over the radial region 512 of the inner surface 506 of the shell wall 502. In one embodiment, the isolating polymeric layer 524 may be any polymer layer or coating that substantially prevents or slows down diffusion of the gelling enhancer 518 into the shell 500.

Figure 10A:
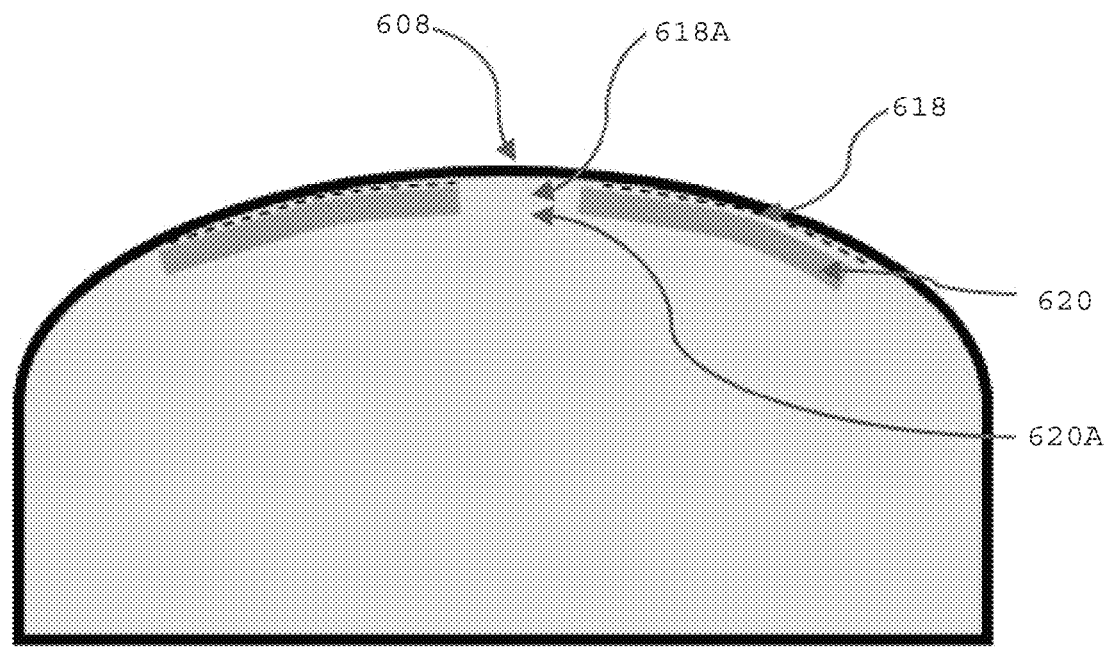
FIG. 10A is a cross-sectional view of an implant shell having a gelling enhancer layer with a geometry that includes a gap of the gelling enhancer at an apex of the shell, in accordance with one embodiment of the present patent application.
Figure 10B:
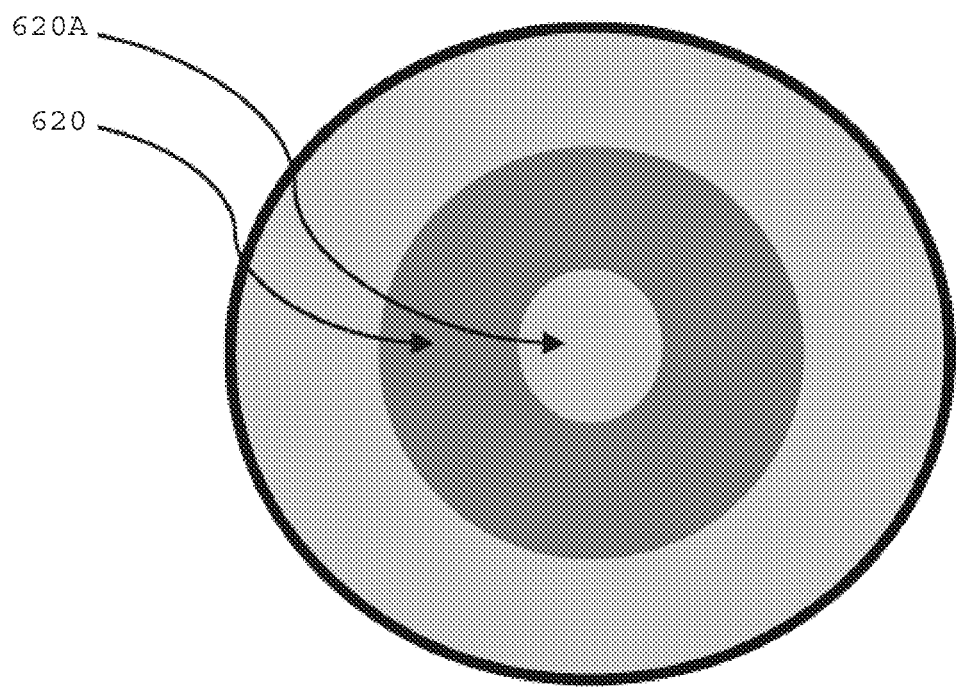
FIG. 10B is a top view of the implant shell shown in FIG. 10A.

Referring FIGS. 10A and 10B, in one embodiment, a shell 600 has an apex 608 with a gelling enhancer layer 618 disposed at the apex 608 and overlying the inside surface of the shell wall 602. The gelling enhancer layer 618 includes a gap 618A formed therein so that there is a void in the gelling enhancer layer 618 at the apex 608 of the shell 600 (i.e., there is no gelling enhancer at the apex 608). The zone 620 of gel material has a higher level of cohesiveness than the remainder of the gel 616. The gel 616 with the lower level of cohesiveness has a region 616A that fills the gap 618A that is present in the gelling enhancer layer 618. The region 616A of the gel 616 does not have the higher level of cohesiveness.

Figure 11:
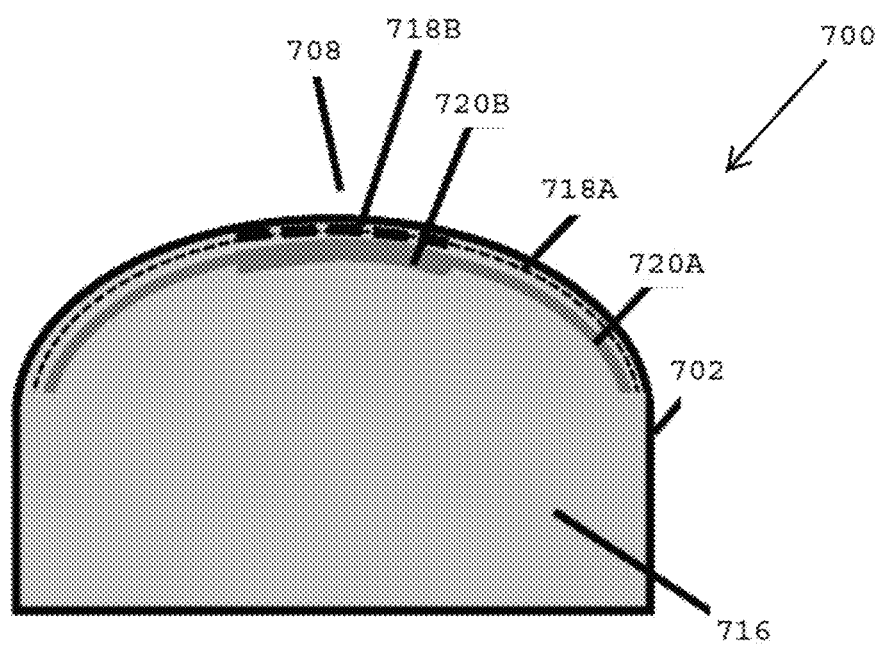
FIG. 11 is a cross-sectional view of an implant shell having a variable amount of gelling enhancer at an apex and a peripheral portion that concentrically surrounds the apex, in accordance with one embodiment of the present patent application.

Referring to FIG. 11, in one embodiment, a shell 700 preferably includes a shell wall 702 having a gelling enhancer layer including an apex portion 718B that is positioned around the apex 708 and a peripheral portion 718A that concentrically surrounds the apex portion 718B. In one embodiment, the apex portion 718B of the gelling enhancer layer preferably contains more gelling enhancer or a higher concentration of gelling enhancer than the peripheral portion 718A of the gelling enhancer layer. In FIG. 11, the apex portion 718B of the gelling enhancer layer is represented schematically by a thicker dashed line and the peripheral portion 718A of the gelling enhancer layer is represented schematically by a thinner dashed line. As a result, upon curing of the gel 716, zones of gel material that have a higher level of cohesiveness are formed in the vicinity of the apex portion 718A and the peripheral portion 718A of the gelling enhancer layer, with the gel in the apex zone 720B being thicker and/or having higher gel cohesiveness than the gel in the peripheral zone 720A (schematically shown in FIG. 11 by a thicker dashed line representing the apex zone 720B). It is to be understood that both the apex zone 720B and the peripheral zone 720A have higher levels of gelling enhancer, respectively, than the bulk gel 716 after curing and thus have higher levels of cohesiveness or higher firmness than the bulk gel 716 after curing. In one embodiment (not shown), gelling enhancer may be present on any or all internal surfaces of the shell wall 702, with the concentration of the gelling enhancer being the same or variable on different portions of the inner surface of the shell wall 702 of the shell 700.

The following examples illustrate how the methodologies disclosed herein work in a two-dimensional model test article, which is a silicone slab with designated locations with higher cross-linked density. Low durometer room temperature vulcanized silicone rubber (RTV) was chosen as the test matrix or as a model curable compound instead of silicone gel due to the limitations of an output testing device, A location having a higher cross-link density provides firmer silicone, which is indicated by using a durometer instrument for testing the hardness of various plastics and rubber.

EXAMPLE 1

Preparation of Catalyst Rich Coating

A silicone coating layer containing an artificially high concentration of platinum catalyst (e.g., Karstedt catalyst) (360 ppm) and polyhydromethylsiloxane cross-linker (6%) was prepared as a two-part kit.

Part A. 45 g of Elkem 55 experimental base (containing vinyl terminated polydimethyl silicone base polymer and fumed silica particles) was mixed with 1.8 g of 2% Karstedt catalyst (Platinum-Divinyltetramethyldisiloxane Complex; Gelest SIP6831.2), 4.5 g of low molecular weight vinyl terminated polydimethyl silicone base polymer (Gelest DMS V21) using a high speed centrifugal mixer (FlackTek DAC150 FV-K) at 3470 rpm for 3 min.

Part B. 45 g of Elkem 55 experimental base (containing vinyl terminated polydimethyl silicone base polymer and fumed silica particles) was mixed with 6 g of polymethylhydrodimethyl siloxane cross linker (Gelest DMS 301) and 0.45 g oil color using a high speed centrifugal mixer (FlackTek DAC150 FV-K) at 3470 rpm for 3 min.

EXAMPLE 2

Figure 12A:
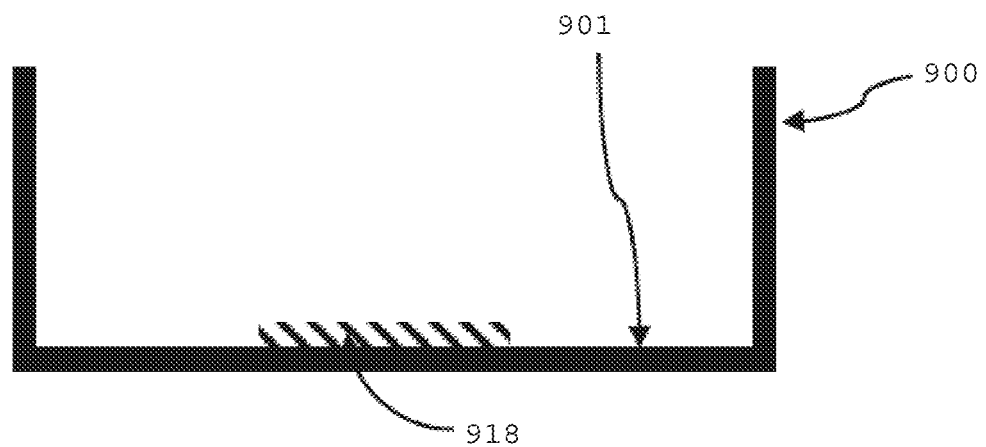
FIG. 12A is a cross-sectional view of a container having a bottom surface and a gelling enhancer rich composition applied onto the bottom surface of the container, in accordance with one embodiment of the present patent application.
Figure 12B:
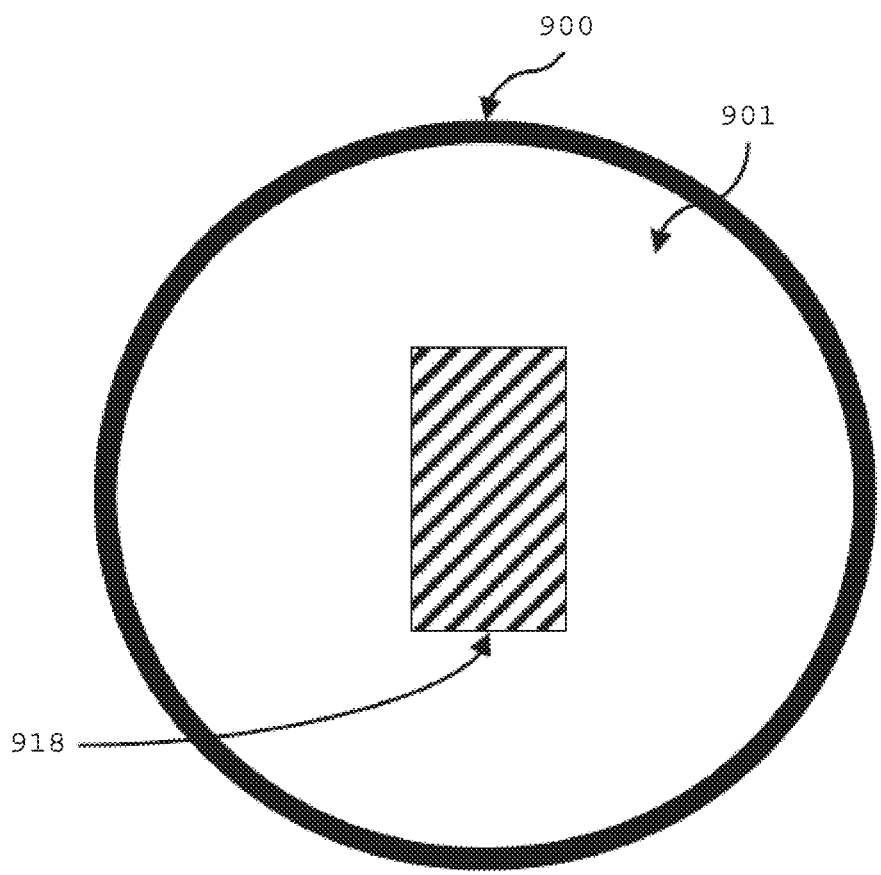
FIG. 12B is a top view of the container and the gelling enhancer rich composition shown in FIG. 12A.

Preparation of Bulk Curable Matrix Containing Low Concentration of Catalyst: Preparation of Testing Samples Having Relatively Lower Durometer of Bulk Material Referring to FIGS. 12A and 12B, in one embodiment, a container 900 has a bottom surface 902. In one embodiment, a pre-mixed catalyst rich two-part composition (Part A and Part B) of Example 1 is applied onto the bottom surface 902 of the container 900, which may be a PTFE-coated (non-stick) Petri dish shaped container. In one embodiment, a catalyst rich strip 918 having dimensions of about 3.5 cm×6.5 cm may be applied approximately in the middle of the bottom surface 902 of the container 900. In one embodiment, the thickness of the catalyst-rich coating strip layer 918 may be approximately 0.3 mm.

Figure 12C:
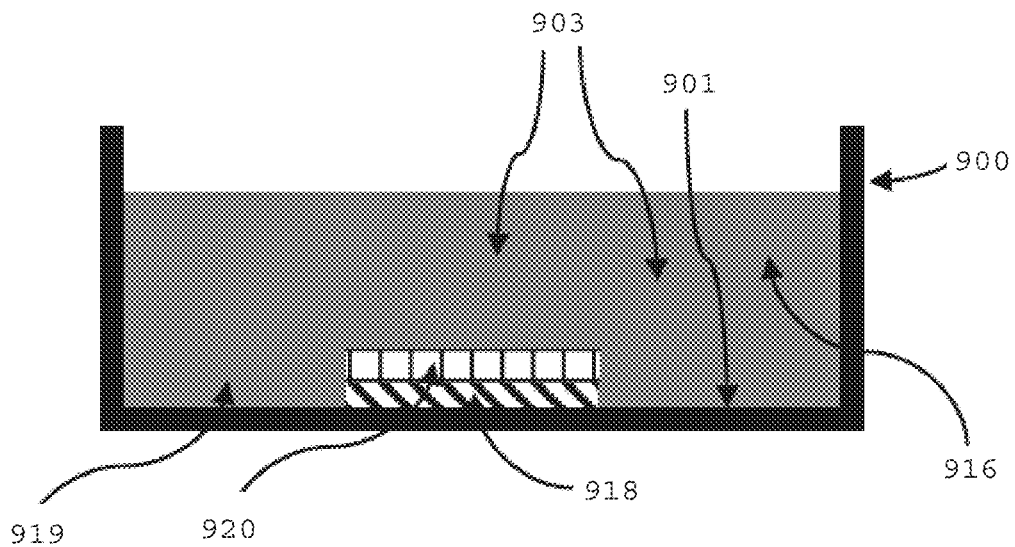
FIG. 12C shows a cross-sectional view of the container of FIGS. 12A and 12B with a casted curable composition inside the container for forming a silicone slab, in accordance with one embodiment of the present patent application.

In one embodiment, the curable compounds may be prepared and tested as follows. 42.5 g of Elkem Silbione RTV (room temperature vulcanized silicone rubber) 4420 QC component A is mixed with 42.5 g of a Elkem Silbione RTV 4410QC component B using a high speed centrifugal mixer (FlackTek DAC150 FV-K) at 3470 rpm for one minute. The above-identified materials are commercially available and already contain pre-mixed catalyst and cross-linker (in a concentration substantially lower than Example 1). The prepared RTVs are preferably refrigerated to approximately 10 degrees C. prior to their mixing and casted into the container 900 having the catalyst rich strip 918 as shown in FIG. 12C so that the added curable RTV mixture 903 covers the bottom of the container 900 (e.g., a Petri dish) and covers both the crosslinker and catalyst rich strip area 918 and areas 919 with no extra crosslinker and catalyst. In one embodiment, a test specimen in a form of a slab having a thickness of about 6 mm is formed after about three hours of cure at ambient temperature conditions (20-25 C). As shown, a zone 920 of RTV exposed to higher crosslinker and catalyst concentrations and having higher firmness vs. bulk RTV 916 will form proximal to the catalyst rich strip 918 after curing.

EXAMPLE 3

Preparation of Bulk Curable Matrix Containing Low Concentration of Catalyst: Preparation of Testing Samples Having Relatively Higher Durometer of Bulk Material Similar to the Example 2 above, a pre-mixed catalyst rich two-part composition (Part A and Part B) of Example 1 is preferably applied onto the bottom surface 902 of a PTFE-coated (non-stick) Petri dish shaped container 900, and a catalyst rich strip 918 having dimensions of about 7.5 cm×2.5 cm is applied approximately in the middle of the bottom surface 902 of the dish 900. In one embodiment, the thickness of the Example 1 crosslinker and catalyst-rich coating strip layer 918 is approximately 0.3 mm.

In one embodiment, the curable compounds may be prepared and tested as follows. 42.5 g of a Elkem Silbione RTV (room temperature vulcanized silicone rubber) 4420 QC component A is preferably mixed with 42.5 g of a Elkem Silbione RTV 4420QC component B using a high speed centrifugal mixer (FlackTek DAC150 FV-K) at 3470 rpm for one minute. The prepared RTVs are preferably refrigerated to approximately 10 degrees C. prior to their mixing and casting into the container/dish 900 having the catalyst rich strip 918 as shown in FIG. 12C so that the added curable RTV mixture 903 covers the bottom of the Petri Dish and covers both the crosslinker and catalyst rich strip area 918 and areas 919 with no extra catalyst or crosslinker. The test specimen in a form of slab with approximately 6 mm thickness was formed after three hours of cure at ambient temperature conditions (about 20-25 C). As shown, the zone 920 of RTV exposed to higher crosslinker and catalyst concentrations and having higher firmness vs. bulk RTV 916 is then forming proximal to the crosslinker and catalyst rich strip 918 after curing.

Performance Testing.

Figure 12D:
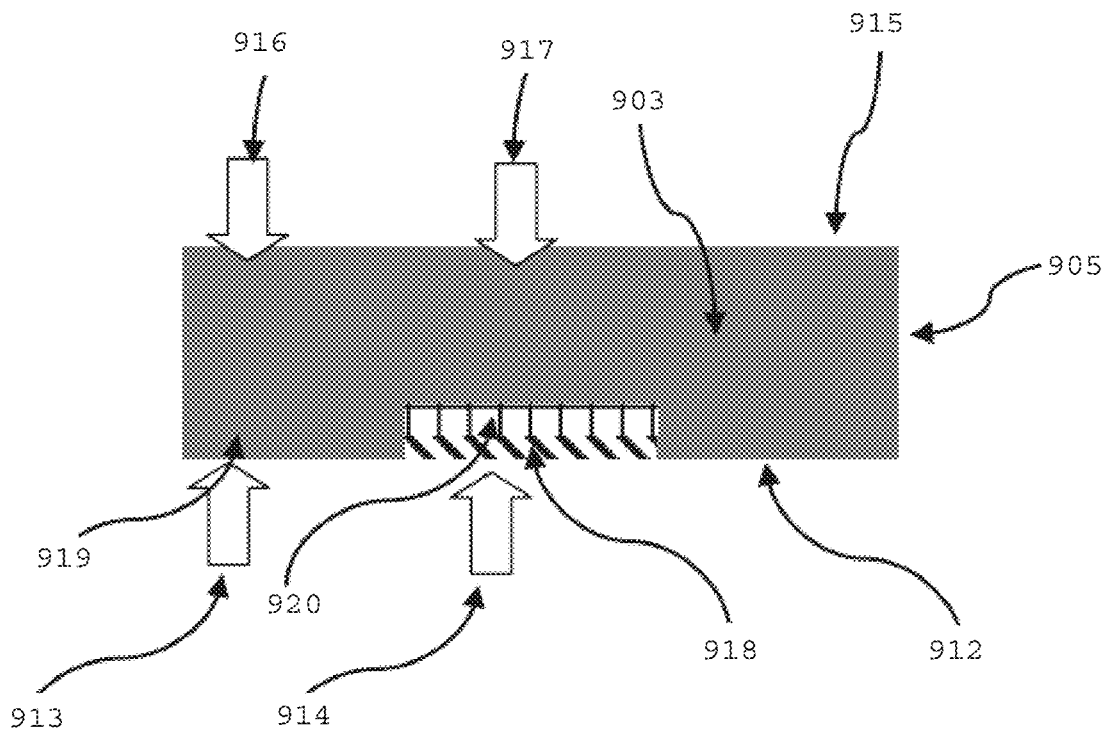
FIG. 12D is a cross-sectional view of a cured silicone slab that has areas for testing, in accordance with one embodiment of the present patent application.

Softness or cohesiveness test. In one embodiment, cured silicone slabs formed via Examples 2 and 3 may be removed from the Petri Dish. In FIG. 12D, the cured slabs 905 are shown schematically after removal from the container 900 (FIG. 12C) for testing in the form of round slabs 905 having a thickness of about 6 mm.

Softness tests on silicone slabs were performed on Examples 2 and 3 following ASTM D2240, using a Rex Shore M durometer gauge. The cured RTV mixture 903 was tested for softness or durometer at several positions. Bottom side 912 of slab 905 was tested at the area of zone 920 where extra crosslinker and catalyst strip 918 is present with testing position shown by arrow 914. Bottom side 912 of the slab 905 was also tested in the area with no extra crosslinker and catalyst 919 with testing position shown by arrow 913.

Top side 915 of slab 905 was tested at the area above zone 920 opposite crosslinker and catalyst strip 918 with testing position shown by arrow 917. Top side 915 of slab 905 was also tested in the area not opposite crosslinker and catalyst strip 919 with testing position shown by arrow 916.

Thus gelling enhancer coated and uncoated regions of the slab were measured on both sides as described above. Five reading were recorded and the results are summarized in the table shown in FIGS. 13 and 15. FIGS. 14A and 14B show a Rex Shore M durometer gauge 640 that may be used for testing both the coated and uncoated regions of the silicone slab.

FIG. 13 shows the results obtained by measuring the bottom side 912 of slab 905 in position 914 "coated region" and position 913 "uncoated region" for Examples 2 and 3. As seen, significantly firmer or high durometer measurements are observed in the areas proximal to gelling enhancer coating or "coated region" 914 vs. position 913 "uncoated region".

FIG. 15 shows the results obtained by measuring top side 915 of slab 905 in position 917 "coated region" and position 916 "uncoated region" for Examples 2 and 3. As seen, no effects on firmness or durometer measurements are observed on the cured material that is remote from the gelling enhancer coating, for positions that are either opposite or not opposite gelling enhancer 918.

The testing results indicate the gelling enhancer coated region has substantially higher durometer (firmness) or lower softness compared to the uncoated regions of the slabs in immediate proximity to gelling enhancer, which is due to the increment of cross link density in the coated region induced by the leach out of active components in the Example 1 gelling enhancer coating layer into its surrounding area.

The softness of the uncoated side of the slabs, i.e., side opposite the side where gelling enhancer is applied for both examples, shows no difference (within error of the measurement) between the coated area and uncoated regions. In other words, the data indicates that further from the zone immediately adjacent the gelling enhancer, there is no effect on the softness or cohesiveness of the gel and bulk gel is not affected, i.e., only the gel zone proximal to the gelling enhancer is affected and acquires higher cohesiveness or firmness. This indicates the localized effect on the increment of cross link density. This also proves that controlling cross link density along the depth of silicone slabs may be achieved using the methods disclosed herein.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of making an implantable prosthesis comprising:
applying a gelling enhancer layer over an inner surface of an anterior wall of a silicone shell, said silicone shell including said anterior wall and a posterior wall that surround an interior volume of said silicone shell;
filling the interior volume of said silicone shell with a silicone gel;
after the filling step, thermally curing said silicone gel disposed within the interior volume of said silicone shell, wherein said cured silicone gel that is located within a zone that is in the vicinity of said gelling enhancer layer has a higher level of cohesiveness than said cured silicone gel that is located outside said zone; and
wherein said zone of said cured silicone gel having the higher level of cohesiveness has a thickness of 2-10 mm.

2. The method as claimed in claim 1, wherein the applying the gelling enhancer layer step comprises:
applying said gelling enhancer layer to a first surface of an isolating polymeric layer; and
applying a second surface of said isolating polymeric layer to the inner surface of said anterior wall of said silicone shell, wherein said isolating polymeric layer is disposed between the inner surface of said anterior wall of said silicone shell and said gelling enhancer layer.

3. The method as claimed in claim 1, wherein said gelling enhancer layer comprises a gelling enhancer, and wherein said cured silicone gel that is located outside said zone has a first concentration level of said gelling enhancer and said cured silicone gel that is located within said zone has a second concentration level of said gelling enhancer that is 5%-300% greater than the first concentration level of said gelling enhancer.

4. The method as claimed in claim 1, further comprising disposing an isolating polymeric layer between the inner surface of said silicone shell and said gelling enhancer layer, wherein said isolating polymeric layer is configured to slow down diffusion of said gelling enhancer layer in said gelling enhancer layer into said silicone shell that is in the vicinity of said gelling enhancer layer.

5. The method as claimed in claim 4, further comprising:
applying said gelling enhancer layer to a first surface of said isolating polymeric layer; and
applying a second surface of said isolating polymeric layer to the inner surface of said wall of said silicone shell.

6. The method as claimed in claim 1, wherein after curing said silicone gel, said cured silicone gel that is located within said zone is more rigid than said silicone gel that is located outside said zone.

7. The method as claimed in claim 1, wherein said gelling enhancer is a catalyst, a crosslinker, or a mixture thereof.

8. The method as claimed in claim 7, wherein said catalyst is a Karstedt catalyst comprising an organoplatinum compound derived from divinyl-containing disiloxane and selected from the group consisting of Pt2[(Me2SiCH=CH2)20]3; Pt2(1, 1,3,3-tetramethyl-1, 3-divinyldisiloxane)3 and Platinum(0)-1,3-divinyl-1, 1,3,3-tetramethyldisiloxane.

9. A method of making an implantable prosthesis comprising:
applying a gelling enhancer layer over an inner surface of a wall of a silicone shell, said silicone shell including anterior and posterior walls that surround an interior volume of said silicone shell;
filling the interior volume of said silicone shell with a silicone gel material;
after the filling step, curing said silicone gel material disposed within the interior volume of said silicone shell, wherein said cured silicone gel material that is located within a zone that is in the vicinity of said gelling enhancer layer has a higher level of cohesiveness than said cured silicone gel material that is located outside said zone; and
wherein said zone of said cured silicone gel material having the higher level of cohesiveness has a thickness of 2-10 mm.

10. The method as claimed in claim 9, wherein said gelling enhancer layer covers the inner surface of said anterior wall of said silicone shell.

11. The method as claimed in claim 9, wherein said silicone shell comprises an apex, a base, a radius located between said apex and said base, and a dome extending between said apex and said radius.

12. The method as claimed in claim 11, wherein said gelling enhancer layer covers said apex of said silicone shell.

13. The method as claimed in claim 11, wherein said gelling enhancer layer covers said dome of said silicone shell.

14. The method as claimed in claim 11, wherein said gelling enhancer layer covers said radius of said silicone shell.

15. The method as claimed in claim 9, wherein said gelling enhancer layer comprises a
    gelling enhancer, and wherein said cured silicone gel material that is located outside said zone has a first concentration level of said gelling enhancer and said cured silicone gel material that is located within said zone has a second concentration level of said gelling enhancer that is 5%-300% greater than the first concentration level of said gelling enhancer.

16. A method of making an implantable prosthesis comprising:
    obtaining a silicone shell having an outer wall that surrounds an interior volume of said silicone shell;
    covering at least a portion of an inner surface of said outer wall of said silicone shell with a gelling enhancer layer comprising a gelling enhancer,
    after the covering step, filling the interior volume of said silicone shell with a curable silicone gel material;
    after the filling step, curing said silicone gel material, wherein said cured silicone gel material that is located within a zone that is in the vicinity of said gelling enhancer layer has a higher level of cohesiveness than said cured silicone gel material that is located outside said zone; and
    wherein said zone of said cured silicone gel having the higher level of cohesiveness has a thickness of 2-10 mm.

17. The method as claimed in claim 16, wherein the covering step comprises:
    applying said gelling enhancer layer to a first surface of an isolating polymeric layer; and
    after the applying said gelling enhancer layer, applying a second surface of said isolating polymeric layer to the inner surface of said anterior wall of said silicone shell so that said isolating polymeric layer is disposed between the inner surface of said outer wall of said silicone shell and said gelling enhancer layer.

\* \* \* \* \*